(12) United States Patent
Mas et al.

(10) Patent No.: US 8,398,591 B2
(45) Date of Patent: Mar. 19, 2013

(54) ASPIRATION CATHETER HAVING VARIABLE VOLUME DISTAL SUCTION CHAMBER

(75) Inventors: Juan-Pablo Mas, Somerville, MA (US); Vincent J. Cangialosi, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 857 days.

(21) Appl. No.: 12/108,125

(22) Filed: Apr. 23, 2008

(65) Prior Publication Data

US 2009/0270808 A1   Oct. 29, 2009

(51) Int. Cl.
*A61M 1/00* (2006.01)

(52) U.S. Cl. ........................................ 604/119

(58) Field of Classification Search ............ 604/19, 604/96.01, 103.05, 103.06, 103.09, 118, 604/119, 121, 35, 173, 187, 20, 22; 606/192, 606/194; 623/1.11
See application file for complete search history.

(56) References Cited

U.S. PATENT DOCUMENTS

| | | | |
|---|---|---|---|
| 5,423,742 A | 6/1995 | Theron | |
| 5,728,067 A | 3/1998 | Enger | |
| 5,919,145 A | 7/1999 | Sahatjian | |
| 6,022,336 A * | 2/2000 | Zadno-Azizi et al. | ... 604/101.05 |
| 6,059,745 A | 5/2000 | Gelbfish | |
| 6,422,988 B1 | 7/2002 | Bradshaw et al. | |
| 6,530,947 B1 | 3/2003 | Euteneuer et al. | |
| 6,558,401 B1 * | 5/2003 | Azizi | ............ 606/159 |
| 6,743,208 B1 | 6/2004 | Coyle | |
| 2005/0245894 A1 * | 11/2005 | Zadno-Azizi | ............ 604/509 |
| 2008/0312672 A1 | 12/2008 | Bonnette et al. | |

OTHER PUBLICATIONS

Rioufol et al "Large Tube Section is the Key to Successful Coronary Thrombus Aspiration: Findings of a Standardized Bench Test," Catheterization and Cardiovascular Interventions; vol. 67; pp. 254-257 (2006).

* cited by examiner

*Primary Examiner* — Christopher D Koharski

(57) ABSTRACT

An aspiration catheter is provided in which rapid withdrawal of a piston disposed within a distal region of a catheter lumen creates a sudden pressure drop for ingestion of intravascular matter into the catheter lumen through a distal port while avoiding large losses of suction common with catheters having long aspiration lumens. Conventional aspiration using the same catheter can subsequently complement the procedure by fully removing the ingested matter from the catheter.

6 Claims, 5 Drawing Sheets

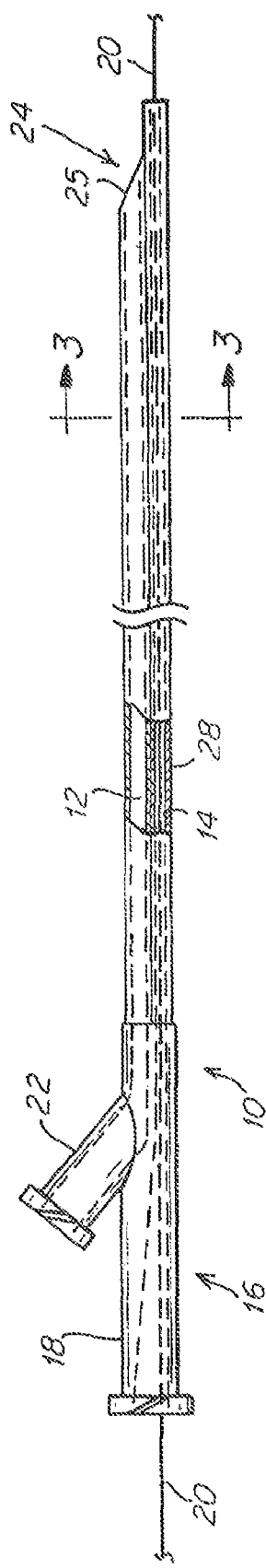
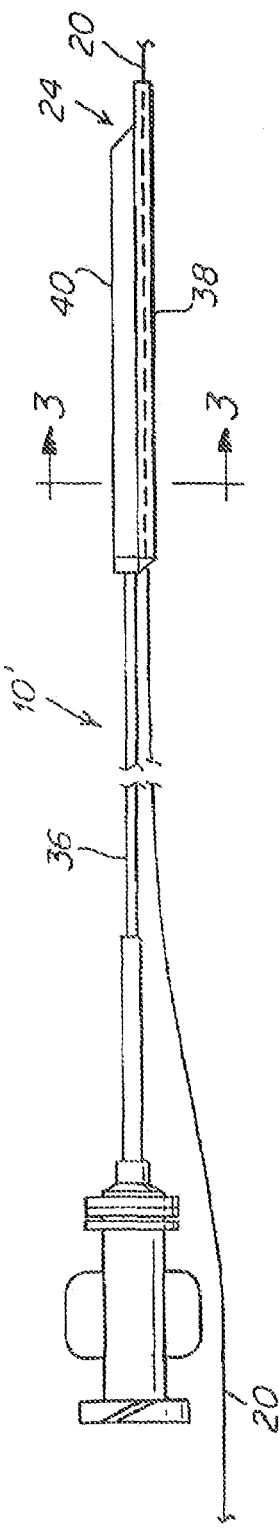

ASPIRATION CATHETER HAVING VARIABLE VOLUME DISTAL SUCTION CHAMBER

FIELD OF THE INVENTION

The invention relates to aspiration catheters for removal from a blood vessel of thrombotic, atherosclerotic or particulate matter, whether it is adherent to the wall of the blood vessel or suspended in the blood.

BACKGROUND OF THE INVENTION

Aspiration catheters are used commonly in connection with interventional vascular procedures such as angioplasty, atherectomy, stent placement, and the like to aspirate debris that may result from an interventional procedure. They also are useful in removing thrombus (clot masses) that may be present in a blood vessel before the interventional catheterization procedure is initiated and also are used to remove clots whether or not other intravascular procedures are intended or have been performed. Such procedures are referred to as aspiration thrombectomy or aspiration embolectomy. The existence of such thrombotic material in the vessel may present significant medical risk if the clot migrates downstream with the blood flow. Thrombus may also form on the luminal wall of the vessel and cause a clinically significant, even a total occlusion. The different types of material that are aspirated by catheters will be variously referred to hereinafter as clot or intravascular material or intravascular matter.

The aspiration catheter must be of a length sufficient to reach the targeted region of the intravascular site from the location of percutaneous entry into the vascular system. For coronary procedures using percutaneous entry in the region of the groin to access the femoral artery, the length of the catheter is typically of the order of 160 centimeters. If it is determined that aspiration should be performed before an interventional procedure the distal end of the catheter is navigated to the region of intended aspiration, for example, to the location where an intravascular blood clot has been determined to exist. With the distal end of the catheter in position, suction is applied at the proximal end of the catheter to engage the clot by suction to draw the clot into the distal end of the aspiration catheter. The terms suction, vacuum, partial vacuum, reduced pressure and negative pressure are all used interchangeably in the field of medical devices. Typically, the reduced pressure in the aspiration lumen of the catheter is caused by connecting a syringe to the aspiration lumen at the proximal end of the catheter and then retracting the plunger in the barrel of the syringe to build up negative pressure in the aspiration lumen over the length of the catheter.

Among the difficulties that may be encountered in the use of an aspiration catheter is that the amount of suction developed at the distal tip is diminished from that applied at the proximal end of the aspiration lumen as a result of fluid resistance associated with fluid flow through the length of the catheter. The loss of suction may be especially problematic when trying to dislodge and aspirate intravascular material such as a blood clot, particularly a mature clot that has adhered to the inner vascular wall and may resist aspiration.

It would be desirable to provide an aspiration catheter that overcomes the inherent loss of suction over the length of the catheter such that a greater aspirating force can be applied by a catheter distal inlet port directly to the intravascular matter to be aspirated. It is among the objects of the invention to provide such catheters.

SUMMARY OF THE INVENTION

In accordance with the invention, aspiration catheters are provided in which an aspirating force is developed within a small chamber in immediate proximity to the distal end of the catheter. In some embodiments the catheter has a lumen, at least at its distal end, in which a short chamber, in the form of a small distal volume of the lumen, is isolated from more proximal portions of the catheter. A sudden pulse of negative pressure is developed within the small volume. By confining the reduced pressure to a small volume at the distal end of the catheter, the invention avoids pressure losses that otherwise may occur when the suction is developed over the full length of the catheter. The confined volume of reduced pressure is exposed, suddenly, to the material to be aspirated. The sudden exposure of a clot or other intravascular matter to the reduced pressure may create a dislodging force that also draws the matter into the chamber and is believed to have increased dislodging force for adherent material, such as thrombus that may be attached to the vessel wall.

In one embodiment of the invention, the distal end of the catheter includes a lumen having a distal inlet port and a piston-like element located within the distal end of the lumen close to the inlet port. In one mode of operation, the piston is slidable longitudinally within the distal end of the lumen and may be drawn proximally and suddenly by a wire or control rod that is connected to the piston and extends proximally through the catheter to the proximal end of the catheter where it can be operated by the clinician. A variable volume chamber thus is defined at the distal end of the catheter by the piston and the wall of the lumen, the distal end of the catheter lumen being open to the vessel lumen via the inlet port. By drawing the piston proximally and quickly in the lumen, the volume of the small chamber is increased rapidly, causing a sudden, momentary reduction in pressure. It is believed that the momentary, but sharp, pressure drop created at the distal end of the catheter lumen will be of sufficient magnitude to dislodge and ingest intravascular matter that may not respond to the relatively weaker suction that would be available at the lumen distal end if a source of negative pressure were applied, in the conventional manner, at the proximal end of the catheter lumen.

In another embodiment of the invention, the distal chamber includes, at its proximal end, a valved side port in the wall of the catheter that communicates with an aspiration lumen separate from the lumen that defines the distal chamber, and which extends to the proximal end of the catheter. The port is arranged such that it is closed by the piston until the piston has been drawn proximally during its pressure reduction stage sufficiently to expose the side port. The port provides a means by which intravascular matter dislodged and ingested into the chamber by the rapid retraction of the piston then can be aspirated through the port and the aspiration lumen. In this embodiment, the piston can be re-advanced to the distal end of the catheter, closing off the side port and in readiness to effect another cycle of operation.

The embodiment having a separate aspiration lumen may be operated in an alternative mode in which the piston seals the side port while negative pressure may be applied from an external source to extensively evacuate the aspiration lumen, which can serve as a vacuum accumulator within the catheter body. When the negative pressure has reached a desired level, the piston may be withdrawn to suddenly uncover the side port to expose the vascular lumen to a sharp, momentary pressure drop to draw thrombus or other intravascular matter into the catheter.

In another embodiment, the piston may be radially expandable and contractible to operate as a valve that may be selectively opened or closed. In the expanded configuration, the piston forms a slidable, occlusive seal with the inner surface of the lumen. In the contracted configuration, the piston permits flow past the piston. In this embodiment, the catheter may require only a single aspiration lumen that contains the radially expandable piston in the distal end to separate the proximal portion of the lumen from the distal portion that includes the distal chamber. As described in one of the embodiments above, by drawing the piston proximally and quickly in the lumen, the volume of the small chamber is increased rapidly, creating a sudden, momentary, strong suction for ingestion of intravascular matter into the chamber. The piston may then be radially contracted to allow conventional aspiration techniques to draw the matter already taken into the distal chamber proximally past the piston into the proximal portion of the aspiration lumen, and out of the catheter, if so desired. The radially expandable and contractible piston may be left in its expanded configuration and operated as a substitute for the non-contractible piston in the embodiments described above In another embodiment, a substantially stationary valving mechanism is provided to control the exposure of the distal chamber to a sudden suction force. In this embodiment, a piston need not be displaced within the aspiration lumen. The radially expandable and contractible piston described above is one means of providing the stationary valving mechanism. When the piston is expanded to seal against the lumen wall and isolates the proximal portion of the lumen from the distal chamber in readiness for subsequent rapid radial collapse of the piston, negative pressure may be applied from an external source to extensively evacuate the proximal portion of the aspiration lumen, which can serve as a vacuum accumulator. Upon radial collapse of the piston, the negative pressure in the aspiration lumen is exposed suddenly to the vessel lumen through the short distal chamber causing forceful aspiration.

DESCRIPTION OF THE DRAWING

The invention will be appreciated more fully from the following further description, with reference to the accompanying drawings in which are not to scale and include exaggerations for clarity, including:

FIG. 1 is a somewhat diagrammatic illustration of an over-the-wire catheter as may embody the invention;

FIG. 2 is a somewhat diagrammatic illustration of a rapid exchange catheter that may incorporate the invention;

DESCRIPTION OF THE ILLUSTRATIVE EMBODIMENTS

Figure 3:
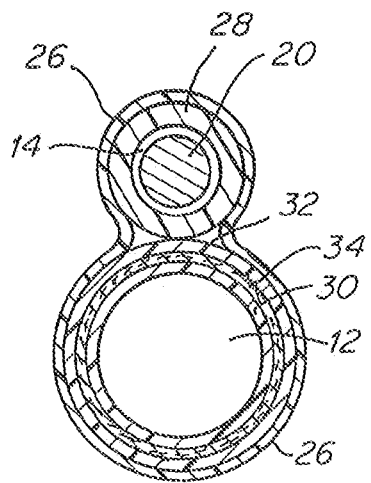
FIG. 3 is a cross-sectional illustration of the catheter as seen along the line 3-3 of FIGS. 1 and 2.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

FIG. 1 illustrates, somewhat diagrammatically, a two-lumen, elongate catheter 10 having an aspiration lumen 12 and a guidewire lumen 14. Both lumens may extend substantially the full length of the catheter, although in some embodiments the aspiration lumen may be limited to the distal region of the catheter. The proximal ends of the lumens may terminate in a Y-fitting 16, one leg 18 of which receives a guidewire 20 and the other leg 22 communicates with the aspiration lumen 12. The distal end 24 of the aspiration lumen terminates in a port 25 and may be beveled, as suggested in FIG. 1 to define a large, oval distal opening.

Catheter 10 may be formed by dual-lumen extrusion. Alternatively, as further illustrated in FIG. 3, which is viewed along the line, 3-3 of FIGS. 1 and 2, for some embodiments, such as the embodiment of rapid exchange catheter 10', the lumens 12, 14 may be constructed from tubes that are attached to each other, for example, by a polymeric film 26 that is heat shrunk about the tubes. The tube 28 that defines the guidewire lumen 14 may be formed from any of a variety of polymeric materials commonly used to construct catheters as known to those familiar with the art. As merely one example, lumen 14 may be 0.016 inch in diameter to slidingly receive a 0.014 inch diameter guidewire, as may typically be used in procedures such as percutaneous transluminal coronary angioplasty. The tube that defines the aspiration lumen 12 may be formed as a multilayer structure including an inner lining tube 30, an outer polymeric tube 32 and a reinforcement layer 34 interposed between the inner and outer tubes 30, 32. The reinforcement layer 34 may be a braided tube formed from any of a variety of metals or polymers in accordance with practices well known to those familiar with the art. As an example, aspiration lumen 12 may be 0.042 inch in diameter. Reinforced braiding is useful in order to provide kink resistance, to increase pushability, viz., longitudinal compressive strength, to transmit rotation from the proximal end to the distal end for steering or directing the catheter tip, and to enhance the resistance of the catheter to collapse from negative pressures within lumen 12. However, a braiding reinforcement may be omitted if the polymer or other material selection and catheter wall dimensions are capable of providing the required physical properties.

FIG. 2 shows another type of aspiration catheter 10' adapted for use in a "rapid exchange" or "single operator" configuration. In this embodiment, the catheter has an aspiration tube 36 and a shortened guidewire tube 38 coupled to the distal portion of the aspiration tube 36. The distal portion 40 of the aspiration tube 36 may be formed from a polymeric material while the more proximal portions of the aspiration tube 36 may be formed from hypotubing. Such construction for rapid exchange catheters is well known to those skilled in the art, as shown, for example, in U.S. Pat. No. 5,728,067 (Enger). The distal portion of the catheter 10' may have the same cross-section depicted in FIG. 3, as seen along the line 3-3 of FIG. 2. The guidewire 20 extends through the guidewire tube 38 with most of the guidewire extending proximally outside of the catheter shaft.

Figure 4:
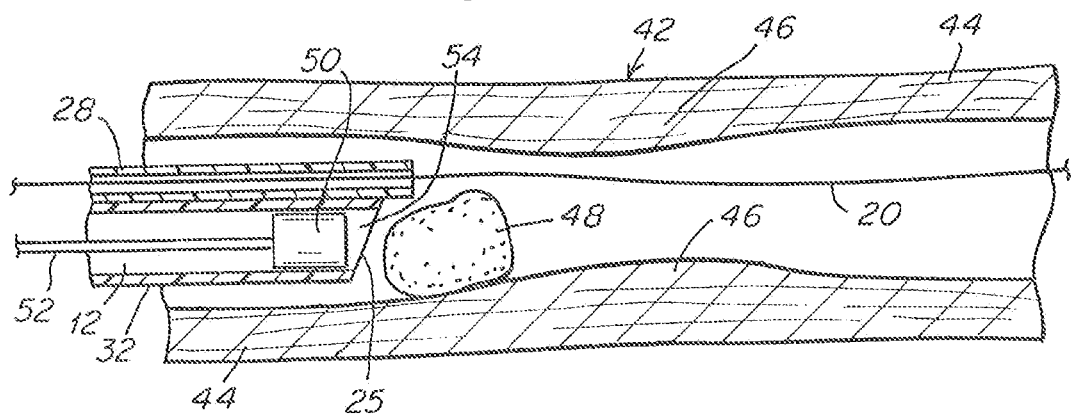
FIG. 4 is a diagrammatic, sectional illustration of the distal end of one embodiment of the invention in a portion of an artery with the distal end of the catheter advanced into close proximity to a clot in readiness to aspirate the clot.
Figure 5:
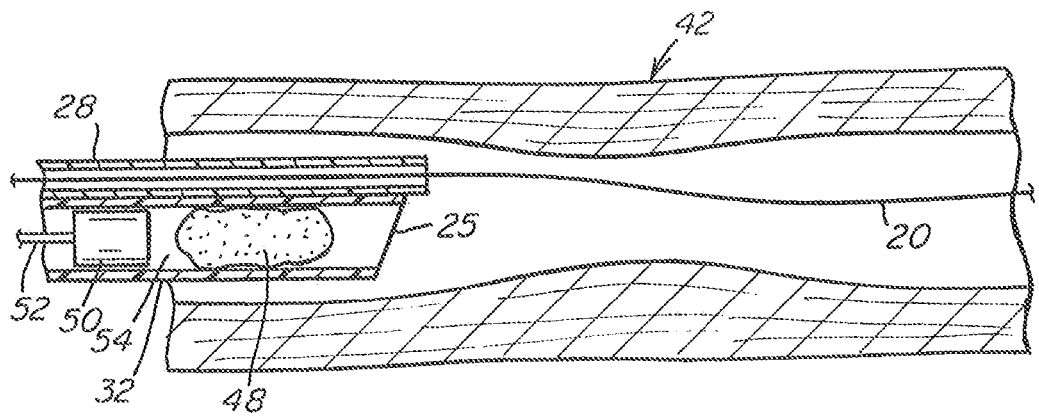
FIG. 5 is a diagrammatic, sectional illustration of the embodiment of FIG. 4 with the piston withdrawn and with the clot loosened and drawn into the catheter.

FIGS. 4 and 5 illustrate, in diagrammatic cross-section, one embodiment of the invention as may be incorporated into a catheter of the type shown in FIGS. 1-3 except that the aspiration lumen need not extend to the proximal end of the catheter. FIG. 4 illustrates the distal end of the catheter in position to aspirate a clot 48 and FIG. 5 shows the device having been operated to ingest the clot 48 through the distal port 25 and into an aspiration chamber 54. FIGS. 4 and 5 show a blood vessel 42 in which the vessel wall 44 has a stenosis 46 that has become narrowed and might present a risk of being obstructed by a clot, shown diagrammatically at 48.

FIG. 4 shows, also diagrammatically, the distal end of an aspiration catheter, similar to those shown in FIGS. 1 and 2, in which the catheter has been modified to include a sealing member, such as a piston 50 slidably disposed within the distal end of the aspiration lumen 12. The piston 50 is connected to a rod 52 that extends from the proximal portion of the piston to the proximal end of the catheter where it can be manipulated by the clinician. Piston 50 and rod 52 may be formed, alternatively, as an elongate, unitary rod of substantially constant diameter having a low friction surface and sufficient flexibility to permit sliding movement within aspiration lumen 12, even when catheter 10 is disposed in tortuous vascular anatomy. The piston 50 may be considered as defining the proximal end of the variable volume chamber 54. The length of chamber 54 may range from 1 cm to 15 cm or longer. As used herein, the term "piston" is intended to refer to any member or device that is slidable within the catheter lumen to define, in cooperation with the luminal wall and the distal end of the lumen, a variable volume chamber and which maintains a seal with the luminal surface to cause a pressure drop in the chamber when the piston is moved to expand the volume of the chamber or is otherwise transformed to isolate the chamber 54 from the more proximal portion of the lumen. The piston may be in the form of a solid member as shown in FIG. 4 or 5 or may take other forms, as described further below.

As shown in FIG. 4 the aspiration catheter will have been advanced to the site of the clot 48 by advancing the catheter over and along a previously placed guidewire 20. The location of the distal end of the catheter with respect to the stenosis 46 and clot 48 may be monitored fluoroscopically to bring the distal end of the catheter in proximity to the clot 48. When the aspiration catheter is so advanced, the piston 50 preferably will be disposed in its most distal position, as suggested in FIG. 4. When the distal end of the catheter is positioned adjacent the clot 48, the rod or wire 52 is pulled to rapidly stroke or displace piston 50 in a proximal direction, thus quickly expanding the volume of chamber 54 and thereby developing a, sudden, reduced pressure at the distal port 25 to ingest the clot into the chamber, as suggested diagrammatically in FIG. 5.

It should be understood that the distal chamber 54 is a variable volume chamber in which the volume can be varied, starting from substantially zero. The piston 50 may be axially translated from a position where it is fully extended to distal port 25 of the catheter, such that the volume of chamber 54 is negligible, to a proximal position that creates a greater swept volume. Thus, the distal chamber may be considered as extending from the distal port 25 to the distal face of the piston 50. Thus, suction within the distal chamber 54 can begin to be created immediately upon initiating proximal displacement of the piston 50, thus overcoming the delay and loss of suction achieved by conventional application of negative pressure to the proximal end of an aspiration catheter.

Figure 6:
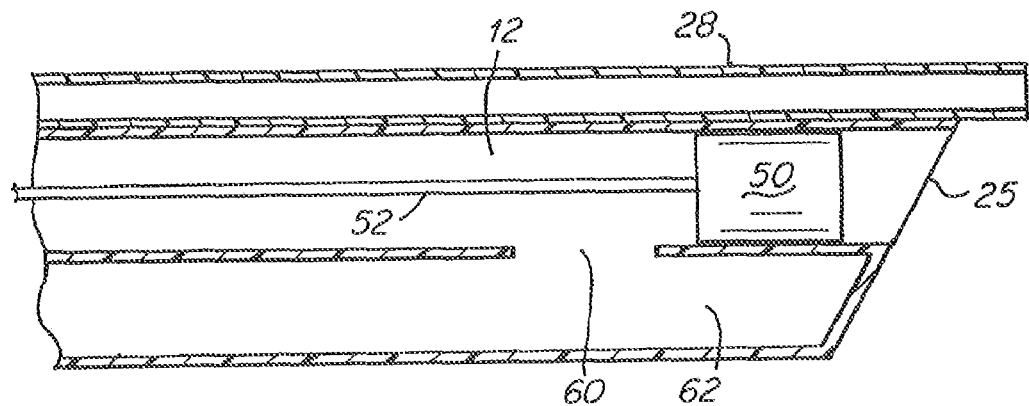
FIG. 6 is a diagrammatic, sectional illustration of another embodiment of the invention in which a valved side port and second lumen are associated with the distal chamber.
Figure 7:
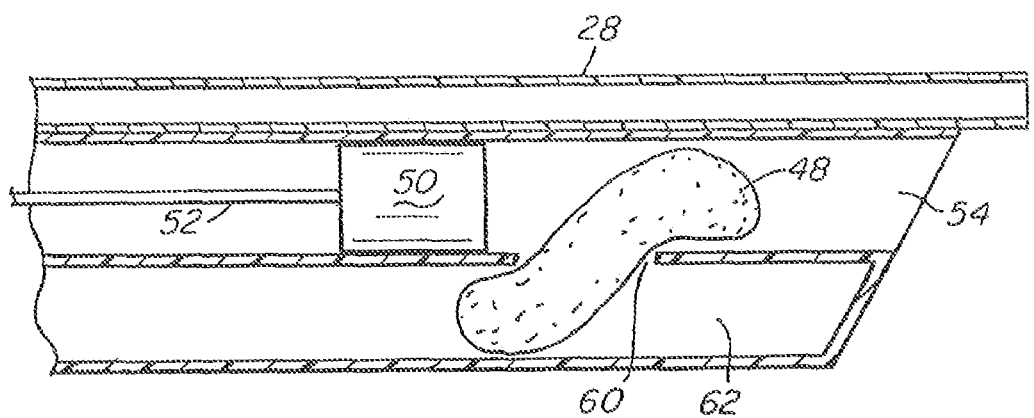
FIG. 7 is an illustration of the embodiment as shown in FIG. 6 with the side port valve open to the distal chamber.

FIGS. 6 and 7 illustrate diagrammatically another embodiment that operates in a manner similar to the embodiment of FIGS. 4 and 5 except that a side port 60 is provided in the luminal wall of the aspiration chamber 54. Piston 50 and side port 60 cooperate to provide a valving mechanism between chamber 54 and another lumen 62, which may extend alongside lumen 12 or surround lumen 12 in a coaxial tube arrangement, as such construction is known to those skilled in the art. The side port 60 is positioned so that when the piston 50 has been drawn fully rearwardly to draw the intravascular matter into the chamber 54, the piston will expose the side port 60. The side port 60 leads to lumen 62 through which the matter may be withdrawn by a conventional aspiration technique, as by applying negative pressure to the proximal end of lumen 62.

Figure 8:
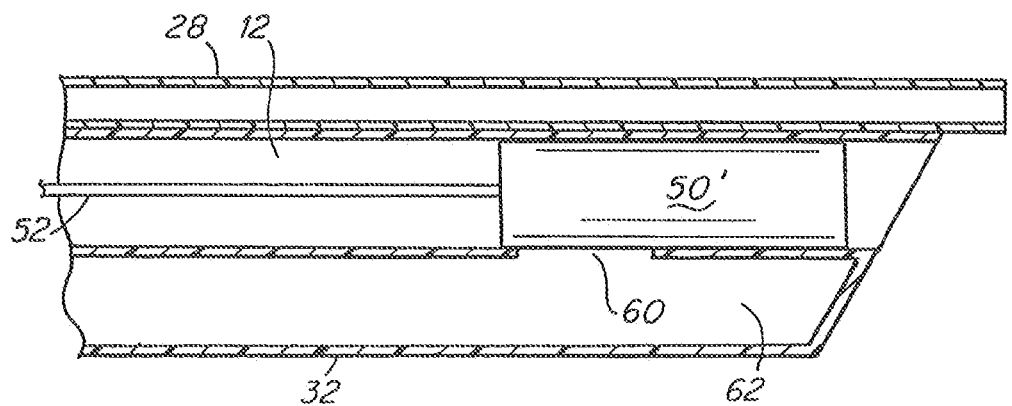
FIG. 8 is a diagrammatic illustration of a modification of the embodiment of FIG. 6 in which the piston and side port of the device are configured to maintain the side port closed to enable the second lumen to function as a vacuum accumulator.
Figure 9:
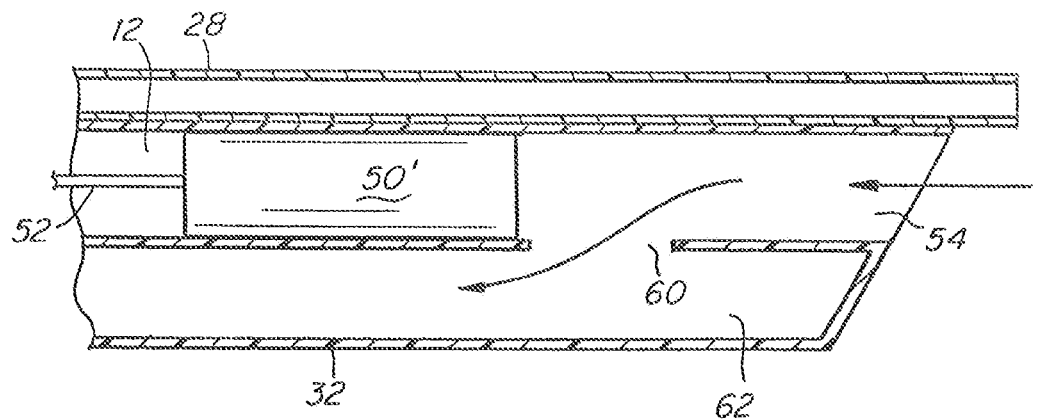
FIG. 9 is an illustration of the modification of FIG. 8 with the piston withdrawn to expose the distal chamber to accumulated vacuum.

In an alternative mode of operating the embodiment illustrated in FIGS. 6 and 7, with piston 50 disposed distally of port 60, negative pressure can be applied to the proximal end of aspiration lumen 62 such that lumen 62 and incidentally, lumen 12, can be evacuated to serve as a vacuum accumulator or reservoir within the aspiration catheter. Thus, when piston 50 is retracted within lumen 12 to permit communication between chamber 54 and aspiration lumen 62 via port 60, the sudden exposure of the accumulated negative pressure to the vascular lumen, through chamber 54 may forcefully ingest intravascular matter through the distal port 25, the side port 60 and possibly into the lumen 62. In this mode, it is not the speed or length of the stroke of piston 50 that are relied on to suddenly generate strong suction at distal port 25. Rather, it is the accumulated negative pressure within lumen 62, which is immediately available to chamber 54 when port 60 is opened by the movement of piston 50, which acts as a sliding valving mechanism. For this reason, port 60 can be located close to distal port 25, if desired, because piston 50 only needs to move the short distance required to open port 60 between lumen 62 and chamber 54. Alternatively, port 60 can be located farther proximally from distal port 25 such that piston 50 can be sharply withdrawn to aspirate intravascular matter, as described above, and then piston 50 can open to port 60 to apply accumulated vacuum within lumen 62 to chamber 54. In a modification of this embodiment (FIGS. 8 and 9), the piston 50' may be longer than the piston 50 of FIGS. 5 and 6 such that the side port 60 can be sealed by the piston 50' to prevent incidental evacuation of lumen 12 while lumen 62 is accumulating negative pressure.

It may be useful to accumulate a lower pressure in the reservoir than can be achieved with a single stroke of a syringe, which, for use with aspiration catheters, typically has a volume of 20 cc or larger. One means of accumulating a lower pressure is to connect the proximal end of aspiration lumen 62 to a central or "wall" vacuum system provided by the hospital or other clinical infrastructure, and which is connected to a remote vacuum pump. Another means of accumulating a lower pressure in the reservoir is to provide a valve such as a stopcock connected between the proximal end of aspiration lumen 62 and a syringe. The accumulator can then be repeatedly evacuated by the syringe, while closing off the stopcock to retain vacuum within the accumulator each time the syringe plunger is reset to zero volume. In this way, the repeated evacuation strokes of the syringe plunger can be used to "pump down" the pressure in the vacuum accumulator to lower and lower pressures.

Figure 10:
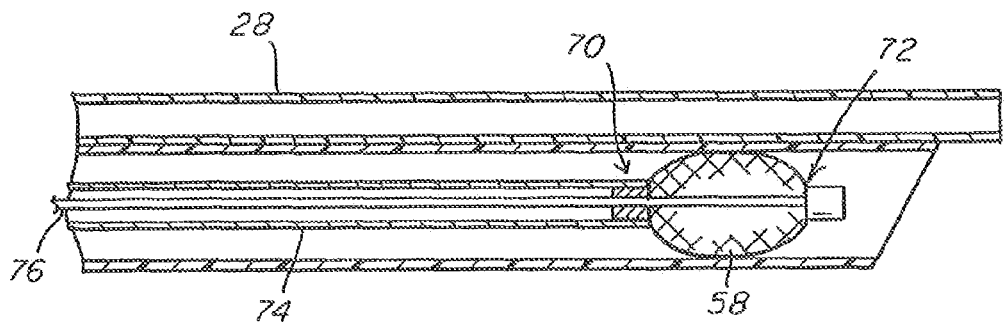
FIG. 10 is a diagrammatic illustration of an embodiment similar to that of FIG. 1 but in which the piston is contractible from a radially expanded configuration to a radially contracted configuration, with the piston in its expanded configuration.
Figure 11:
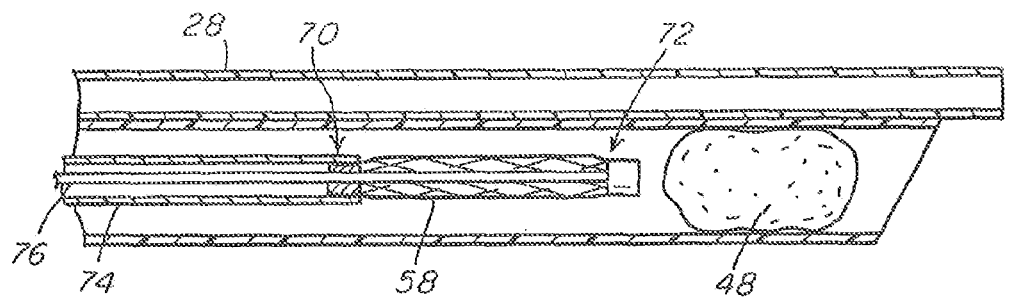
FIG. 11 is a diagrammatic illustration of the embodiment of FIG. 10 with the piston in its radially contracted configuration.

FIGS. 10 and 11 illustrate another embodiment in which the sealing member may comprise a piston 58 defined by a radially expandable and contractible element. In its expanded, or sealing configuration, the piston 58 may function as described above, to be suddenly retracted to create rapid enlargement of the aspiration chamber 54 at the distal end of the catheter so that a brief, but strong suction can be applied to the clot to ingest the clot into the chamber. When the piston is in a contracted (FIG. 11) configuration, the aspiration lumen is open fully from the distal port 25 to the proximal end of the catheter, enabling the already-aspirated material to be drawn proximally beyond the piston 58, as by the conventional technique of applying negative pressure to the proximal end of the lumen. The piston 58 then may be re-expanded into sealed engagement with the lumen of the catheter and the procedure may be repeated if desired.

The embodiment of FIGS. 10 and 11 may be operated in an alternate mode in which the radially expandable and contractible piston 58 serves as a substantially stationary valving mechanism. When in a sealing configuration, piston 58 seals the distal aspiration chamber 54 from the more proximal portions of the aspiration lumen while the proximal portion of the aspiration lumen may be evacuated by connection to an external source of vacuum and maintained at a desired level of negative pressure to function as a vacuum accumulator or suction reservoir, as described above with respect to FIGS. 6-9. When it is desired to perform the aspiration, the piston 58 is contracted radially and suddenly to open the valving mechanism in the aspiration lumen, thus rapidly lowering the pressure at the distal port 25 in the region of the vascular lumen to be aspirated. Upon aspiration of matter into the catheter, the matter may be drawn proximally past piston 58 to within the proximal portion of the aspiration lumen or out of the catheter, if desired. Should another aspiration cycle be desired, the piston 58 may be re-expanded into sealed engagement with the luminal surface of the catheter and vacuum may be accumulated again in the proximal portion of the aspiration lumen for another cycle.

Alternatively, sealing member 58 may be positioned at the distal tip of the aspiration lumen such that the volume of chamber 54 is negligible and sealing member 58 serves solely a valving function, viz. no sliding piston function. In this embodiment, with the valving member 58 in its expanded, sealed configuration, the entire length of the aspiration lumen may be evacuated to generate a reduced pressure that may be accumulated until it is desired to perform the aspiration function. At that point, the valve element is rapidly collapsed to expose the distal port 25 to a sudden suction pulse to aspirate matter into the catheter.

In this mode of operation, wherein piston 58 serves an expandable and contractible valving function, it is important that the piston 58 be operable with rapidity sufficient to rapidly contract its diameter and not to adversely obstruct flow through the aspiration lumen. To that end, a direct mechanical mechanism is preferred to expand or contract the piston 58. It also should be understood that in this mode of operation, the piston 58 may not require rapid withdrawal, or any withdrawal at all, in order to initiate the sudden suction pulse to dislodge thrombus or matter. If desired, however, the piston 58 may be operated in either mode because, when in the expanded configuration, piston 58 may be substituted for either piston 50 or 50', as described above.

The variable profile piston 58 may be formed as a mesh or braided material in a generally tubular configuration having proximal and distal ends 70, 72 that enables the piston to expand when the ends 70, 72 are brought together and to contract to a low profile when the ends of the mesh are urged apart. The mesh may be coated with an appropriate material, such as, for example only, a silicone elastomer that provides good lubricity with the inner surface of the aspiration lumen while also providing a good seal against the surface to facilitate development and retention of suction. The mesh may be expanded by a push-pull arrangement of a tube 74, such as hypotubing and a rod 76 extending through the hypotubing 74. The distal end of the tube 74 may be attached to the proximal end 70 of the tubular mesh and the distal end of the rod 76 may be attached to the distal end 72 of the tubular mesh. Manipulation of the tube and rod effects the change in profile. In other embodiments, different substantially stationary valving mechanisms may be located within a distal region of the catheter to serve the same function as the radially expandable and contractible piston 58. Exemplary valving mechanisms include a poppet valve and a flapper valve. A poppet valve comprises a disc-shaped head for selectively sealing against a ring-shaped seat within the catheter lumen. The position of the head is controlled by an elongate stem extending proximally from the head through the lumen and exiting the catheter. A flapper valve may be similar to the poppet valve except that the head is hinged on one side, as by a flexible plastic "living" hinge, to swing open and closed against the seat.

It should be understood that the foregoing description of the invention is intended merely to be illustrative thereof and that other embodiments, modifications and equivalents may be apparent to those skilled in the art while remaining within the scope of the invention.

We claim:

1. A catheter for aspirating matter from within a blood vessel comprising:
   an elongate shaft with proximal and distal ends and having lumen terminating in a distal port at the distal end of the shaft; and
   a sealing member slidably maintained within the distal region of the lumen and separating the lumen into proximal and distal segments, the distal segment of the lumen comprising a variable volume chamber disposed in communication with the distal port;
   the sealing member being adapted to be rapidly withdrawn in the lumen from a first position to a second, more proximal, position to increase the volume of the distal chamber, thus creating a sudden reduction in pressure within the chamber for causing the matter to be aspirated into the variable volume chamber through the distal port.

2. The catheter as defined in claim 1 wherein the sealing member is configured to be selectively transformable between an expanded profile configuration within the lumen, sealably slidable against an inner surface of the lumen, and a low profile configuration within the lumen having a reduced profile that enables flow from the distal segment of the lumen past the sealing member into the proximal segment of the lumen.

3. The catheter as defined in claim 2 wherein the sealing member has an elongate rod extending proximally therefrom through the lumen and exiting the proximal end of the catheter to permit a clinician to selectively control the axial position of the sealing member within the lumen.

4. The catheter as defined in claim 2 wherein the sealing member is transformable between its expanded and low profile configurations by a mechanical push-pull mechanism operatively connected to proximal and distal ends of the sealing member.

5. The catheter as defined in claim 2 wherein the sealing member comprises an expandable and contractible tubular mesh having proximal and distal ends, the mesh having a low friction flexible outer impermeable layer adapted to seal against the inner surface of the lumen.

6. The catheter as defined in claim 1 further comprising a source of negative pressure attached to the proximal segment of the lumen.

* * * * *